(12) United States Patent
Chou (10) Patent No.: US 10,107,750 B2
(45) Date of Patent: Oct. 23, 2018

(54) DETECTING DEVICE, DETECTING APPARATUS, AND METHOD FOR DETECTING PRESENCE OF SUBSTANCE IN CONTAINER

(71) Applicant: Tien-Ming Chou, Taichung (TW)

(72) Inventor: Tien-Ming Chou, Taichung (TW)

(*) Notice: Subject to any disclaimer, the term of this patent is extended or adjusted under 35 U.S.C. 154(b) by 22 days.

(21) Appl. No.: 15/240,471

(22) Filed: Aug. 18, 2016

(65) Prior Publication Data

US 2017/0261430 A1    Sep. 14, 2017

(30) Foreign Application Priority Data

Mar. 11, 2016   (TW) .............................. 105107470 A (51) Int. Cl.
| | |
|---|---|
| *G01N 21/59* | (2006.01) |
| *G01V 8/12* | (2006.01) |
| *G01D 5/32* | (2006.01) |
| *G01F 23/00* | (2006.01) |

(52) U.S. Cl.
CPC ............... *G01N 21/59* (2013.01); *G01D 5/32* (2013.01); *G01F 23/00* (2013.01); *G01V 8/12* (2013.01); *G01N 2201/0633* (2013.01)

(58) Field of Classification Search
CPC .. G01N 21/59; G01N 2201/0633; G01V 8/12; G01D 5/32; G01F 23/00

USPC ................. 356/432–448, 426–428, 335–343
See application file for complete search history.

(56) References Cited

U.S. PATENT DOCUMENTS

| | | | | | |
|---|---|---|---|---|---|
| 4,402,612 | A | * | 9/1983 | Alexander | G01N 21/9027 348/127 |
| 4,452,759 | A | * | 6/1984 | Takekawa | G01N 21/5911 356/39 |
| 2013/0029407 | A1 | * | 1/2013 | Terazono | G01N 1/31 435/287.2 |

\* cited by examiner

*Primary Examiner* — Tri T Ton
(74) *Attorney, Agent, or Firm* — LeClairRyan (57) ABSTRACT

A detecting apparatus includes a container, and a detecting device including a transmitting module and a receiving module. The transmitting module includes a light-emitting element provided at a first point of the container and operable to transmit a photo signal to propagate toward the container along an optical path. The receiving module includes a light-receiving element provided at a second point of the container and configured to receive the photo signal transmitted through the container. The receiving module is operable to determine whether a substance is present within the container based on receipt of the photo signal. An imaginary tangent plane tangent to the first point is not parallel to an imaginary tangent plane tangent to the second point.

16 Claims, 11 Drawing Sheets

DETECTING DEVICE, DETECTING APPARATUS, AND METHOD FOR DETECTING PRESENCE OF SUBSTANCE IN CONTAINER

CROSS-REFERENCE TO RELATED APPLICATION

This application claims priority of Taiwanese Patent Application No. 105107470, filed on Mar. 11, 2016.

FIELD

The disclosure relates to a detecting device, more particularly to a detecting device, a detecting apparatus, and a method for detecting presence of a substance in a container.

BACKGROUND

Figure 1:
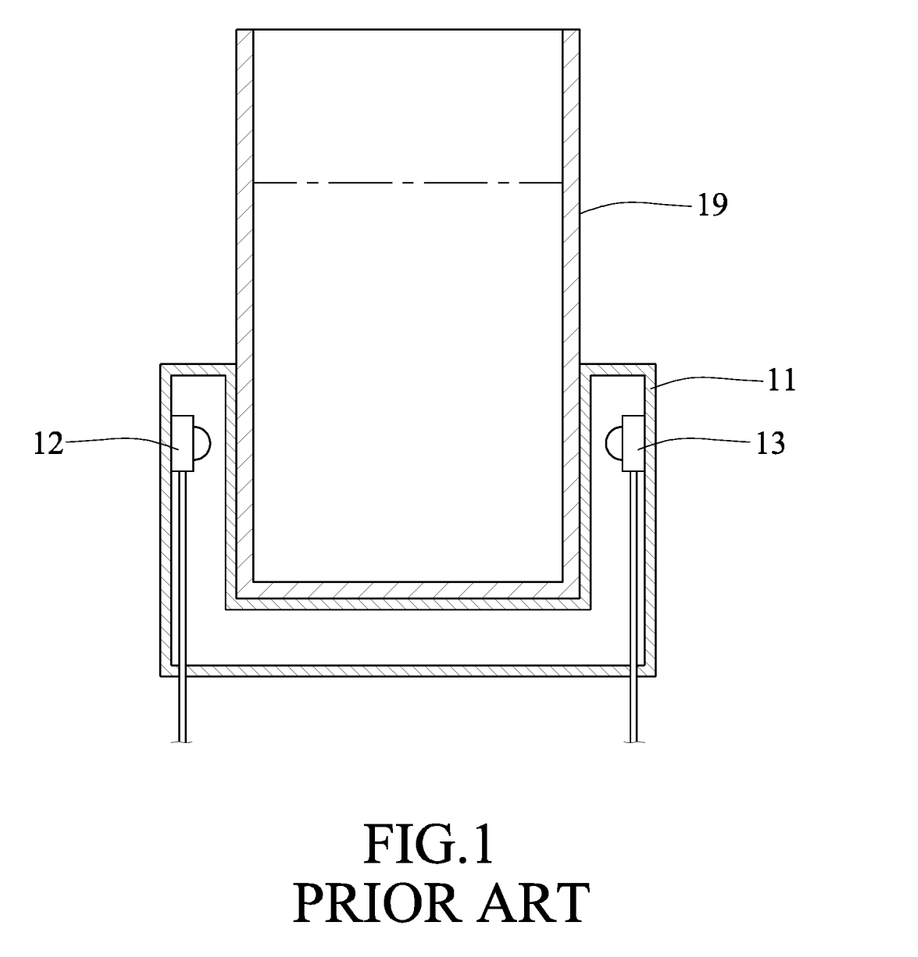
FIG. 1 is a schematic sectional view of a conventional detecting device.

Referring to FIG. 1, a conventional detecting device for detecting presence or level of a substance in a container 19 is shown to include a housing 11 accommodating the container 19, a transmitting module 12 disposed in the housing 11, and a receiving module 13 disposed in the housing 11. The transmitting module 12 is operable to transmit a photo signal to pass through the container 19, and the receiving module 13 is configured to receive the photo signal transmitted from the transmitting module 12 for determining whether the substance is present in the container 19. However, the transmitting module 12 and the receiving module 13 of such conventional detecting device need to be correspondingly disposed on two opposite sides of the container 19, thereby requiring a relatively large space for installation of the same. Moreover, a distance between the transmitting module 12 and the receiving module 13 is relatively long, which may result in false detection due to insufficient strength of the photo signal received by the receiving module 13.

Figure 2:
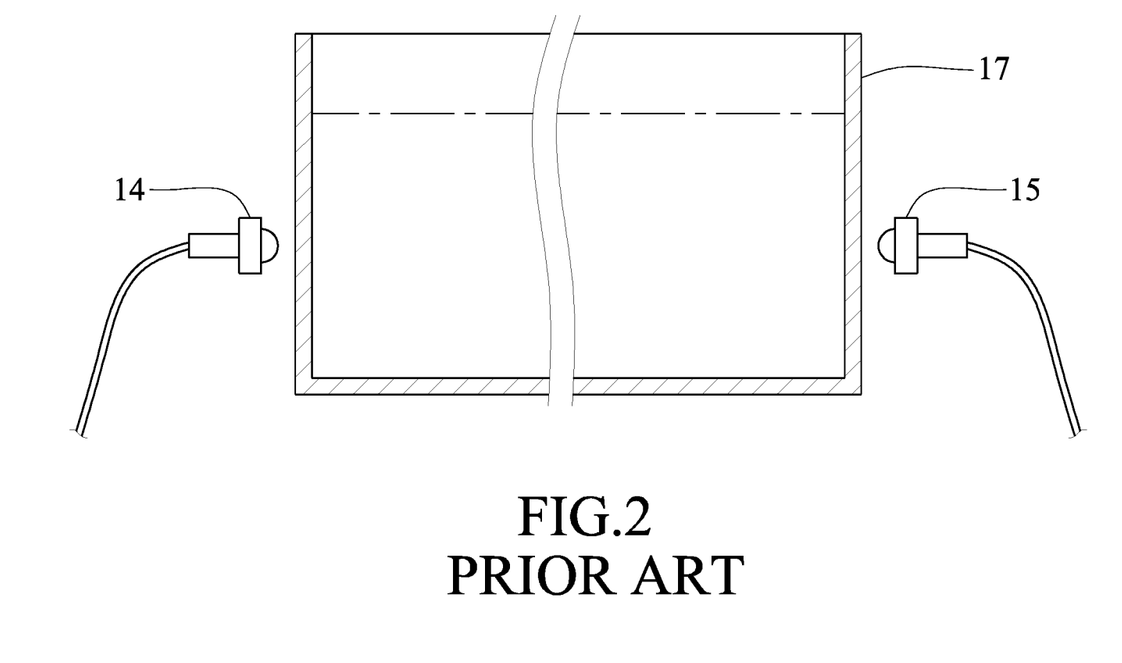
FIG. 2 is a schematic view of another conventional detecting device.

Referring to FIG. 2, another conventional detecting device is disclosed, which includes a laser-emitting module 14 for transmitting a laser signal to pass through a container 17, and a laser-receiving module 15 for receiving the laser signal and for determining whether the substance is present in the container 17. Although utilization of the laser-emitting module 14 and the laser-receiving module 15 provides a greater maximum detecting distance between the laser-emitting module 14 and the laser-receiving module 15 compared with that of the above-mentioned conventional detecting device in FIG. 1, manufacturing costs and energy consumption of the laser-emitting module 14 and the laser-receiving module 15 are relatively high.

SUMMARY

According one aspect of the present disclosure, a detecting apparatus may include a container, and a detecting device including a transmitting module and a receiving module. The container is for receiving a substance. The transmitting module includes a light-emitting element that is provided at a first point of the container and that is operable to transmit a photo signal to propagate toward the container along an optical path. The receiving module includes a light-receiving element that is provided at a second point of the container and that is configured to receive the photo signal transmitted through the container along the optical path. The receiving module is operable to determine whether the substance is present in the optical path within the container based on receipt of the photo signal by the light-receiving element. A first imaginary tangent plane tangent to the first point of the container is not parallel to a second imaginary tangent plane tangent to the second point of the container.

According another aspect of the present disclosure, a detecting device for detecting presence of a substance in a container may include an enclosure, a transmitting module and a receiving module. The enclosure is disposed in the container and has two space-defining planes that cooperatively define a receiving space therebetween. The transmitting module includes a light-emitting element that is received in the enclosure, that is provided at one of the space-defining planes and that is operable to transmit a photo signal to propagate toward the receiving space from the one of the space-defining plane. The receiving module includes a light-receiving element that is received in the enclosure, that is provided at the other one of the space-defining planes and that is configured to receive the photo signal transmitted from the light-emitting element through the receiving space. The receiving module is operable to determine whether the substance is present in the receiving space based on receipt of the photo signal by the light-receiving element.

According to yet another aspect of the present disclosure, a method for detecting presence of a substance in a container includes:

providing a detecting device including a transmitting module including a light-emitting element that is operable to transmit a photo signal, and a receiving module including a light-receiving element that is configured to receive the photo signal;

disposing the light-emitting element at a first point of the container; and disposing the light-receiving element at a second point of the container in such a manner that a first imaginary tangent plane tangent to the first point of the container is not parallel to a second imaginary tangent plane tangent to the second point of the container.

BRIEF DESCRIPTION OF THE DRAWINGS

Other features and advantages of the disclosure will become apparent in the following detailed description of the embodiment (s) with reference to the accompanying drawings, of which.

DETAILED DESCRIPTION

Referring to FIGS. 3 to 9, a first exemplary embodiment of a detecting apparatus according to the present disclosure is shown to include a container 9 (see FIG. 4) for receiving a substance (not shown), and a detecting device including a substrate body 2, a transmitting module 3, and a receiving module 4.

Figure 3:
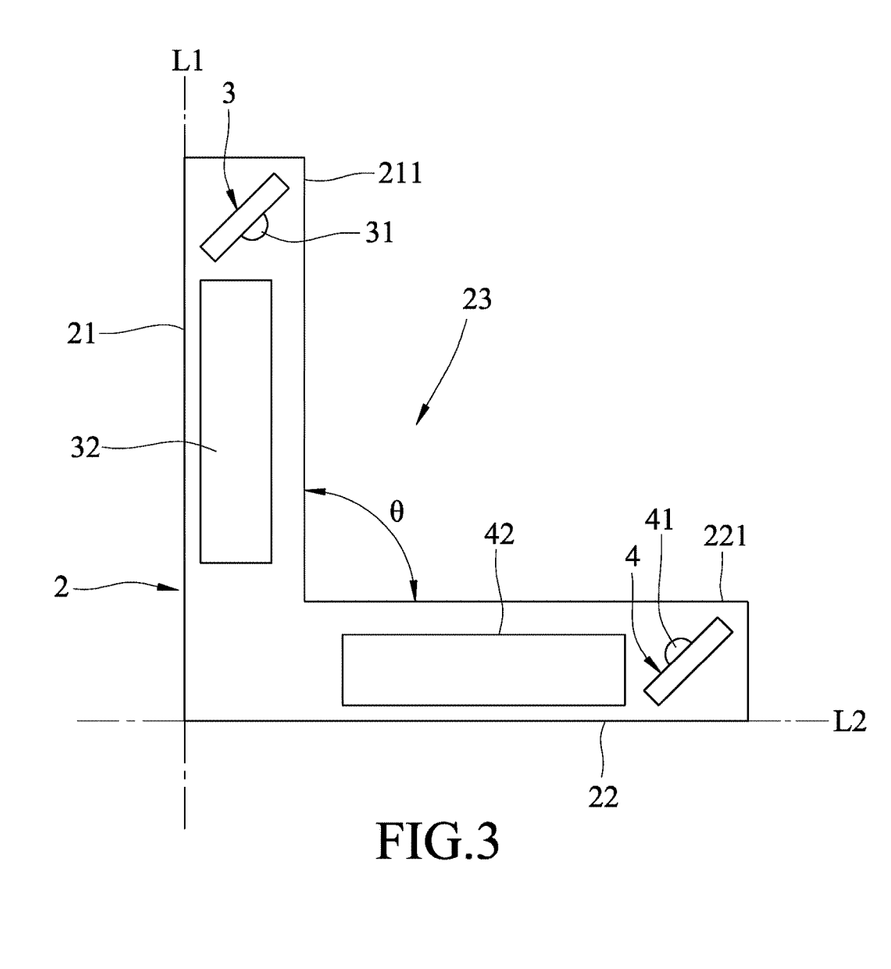
FIG. 3 is a schematic view of a first exemplary embodiment, illustrating a detecting device according to the present disclosure.

The substrate body 2 may be integrally formed as one piece and have first and second side segments 21, 22 respectively extending in first and second directions (L1, L2) as depicted in FIG. 3. The first and second side segments 21, 22 cooperatively define a V-shaped indentation 23 for receiving the container 9 (see FIG. 4). Specifically, the first and second side segments 21, 22 of the substrate body 2 respectively have indentation-defining planes 211, 221 intersecting with each other to define the V-shaped indentation 23. The indentation-defining planes 211, 221 may intersect at an angle (θ) ranging from 45° to 135°. In this embodiment, the angle (θ) between the indentation-defining planes 211, 221 is 90°, and the substrate body 2 is configured into an L-shaped structure as illustrated in FIG. 3.

Figure 4:
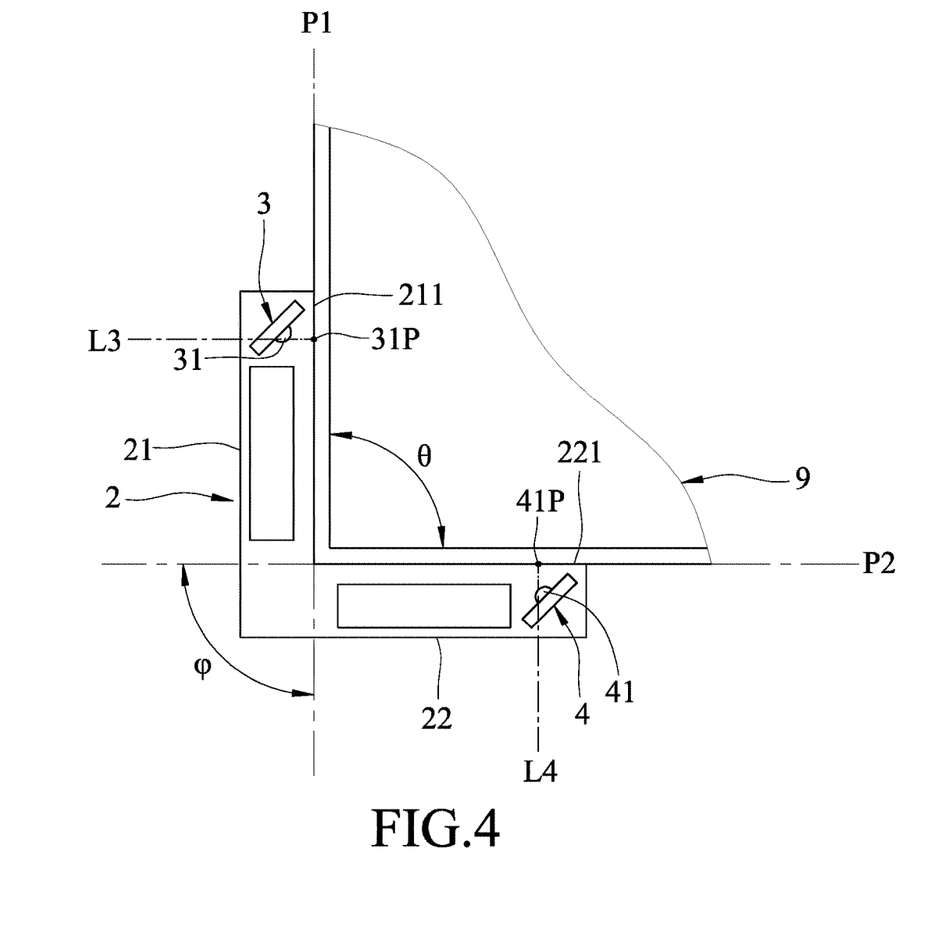
FIG. 4 is a fragmentary schematic view of the first exemplary embodiment, illustrating a detecting apparatus including the detecting device and a container.

The container 9 may be at least partially received in the V-shaped indentation 23 of the substrate body 2 as shown in FIG. 4. It is worth noting that, the container 9 may be partially or fully light-transmissive. It is also worth noting that, the container 9 may be configured in various shapes, e.g., polygonal prisms such as rectangular prisms (see FIGS. 7 and 8) and octagonal prisms (not shown in the figures), or cylinders (see FIG. 9). In such embodiments, the container 9 may have a bottom surface and one or more side surfaces.

The transmitting module 3 of the first exemplary embodiment includes a light-emitting element 31 that is provided at the first side segment 21 of the substrate body 2, and a control element 32 that is electrically coupled to the light-emitting element 31 and that may be provided on the substrate body 2 as shown in FIG. 3. The light-emitting element 31 is operable to transmit a photo signal to propagate toward the V-shaped indentation 23 and the container 9 when the container is received in the V-shaped indentation 23 as illustrated in FIG. 4. The control element 32 is operable to control the light-emitting element 31 to transmit the photo signal. The photo signal in this embodiment may be infrared light or visible light.

The receiving module 4 of the first exemplary embodiment includes a light-receiving element 41 that is provided at the second side segment 22 of the substrate body 2, and a control element 42 that is electrically coupled to the light-receiving element 41 and that may be provided on the substrate body 2 as shown in FIG. 3. The light-receiving element 41 is configured to receive the photo signal transmitted through the container 9 along the optical path, and the control element 42 is operable to determine whether the substance is present in the optical path within the container 9 based on the receipt of the photo signal by the light-receiving element 42. For example, when the photo signal detected by the light-receiving element 41 is weaker in strength than that transmitted by the light-emitting element 31, or when the photo signal is not detected by the light-receiving element 41, the control element 42 determines that the substance is present in the optical path within the container 9.

Figure 5:
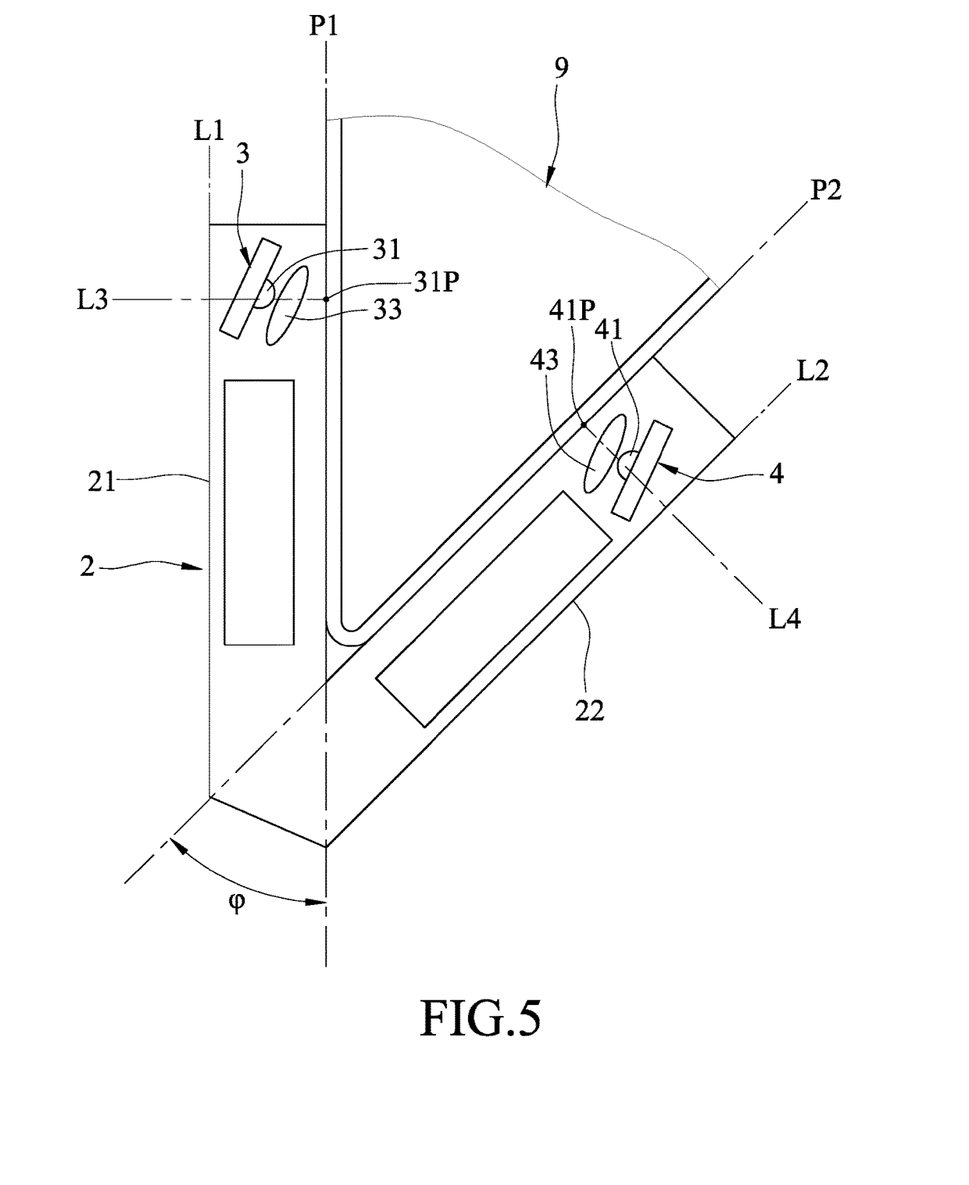
FIGS. 5 and 6 are fragmentary schematic views of the first exemplary embodiment, illustrating various modified detecting devices.
Figure 6:
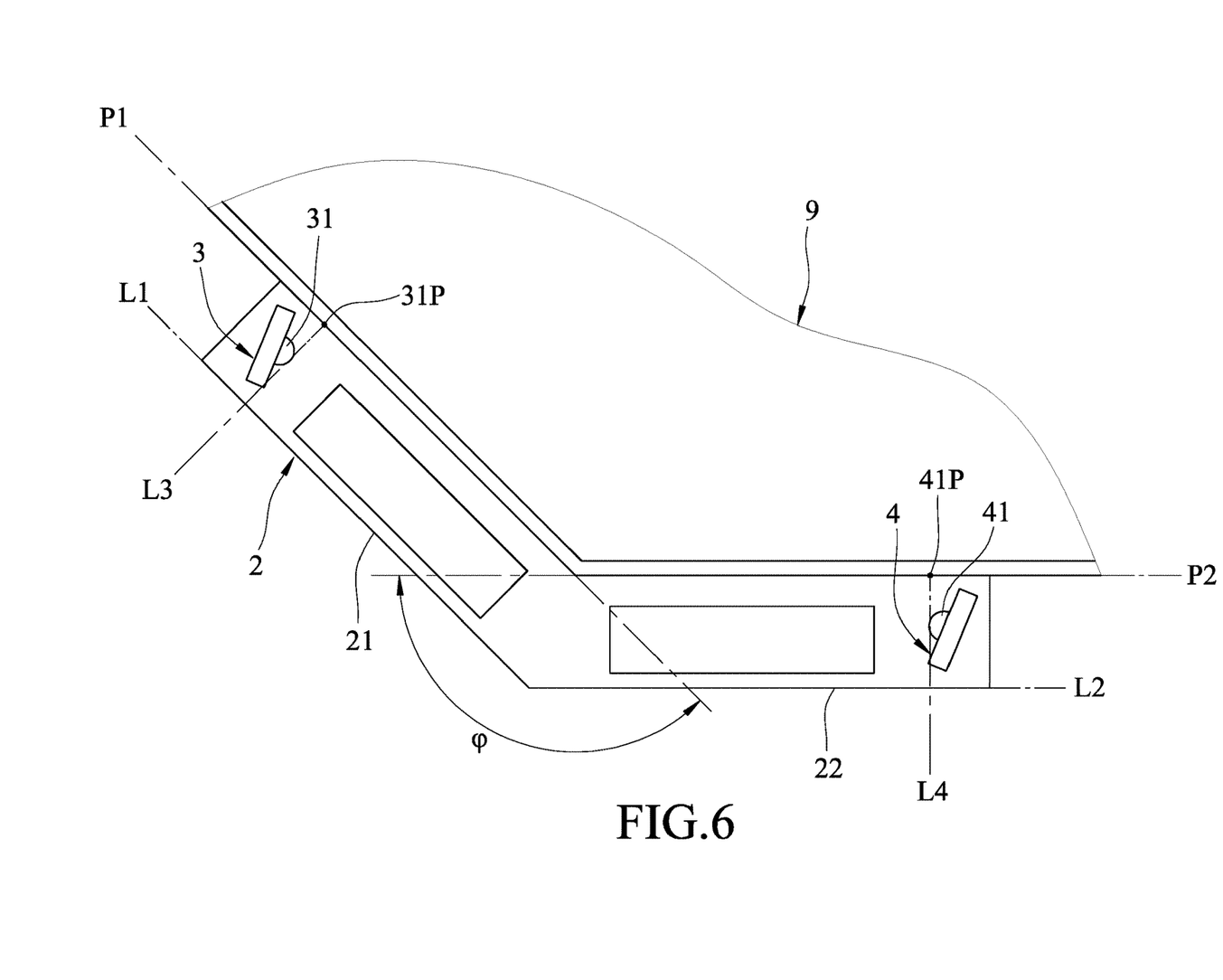
Figure 7:
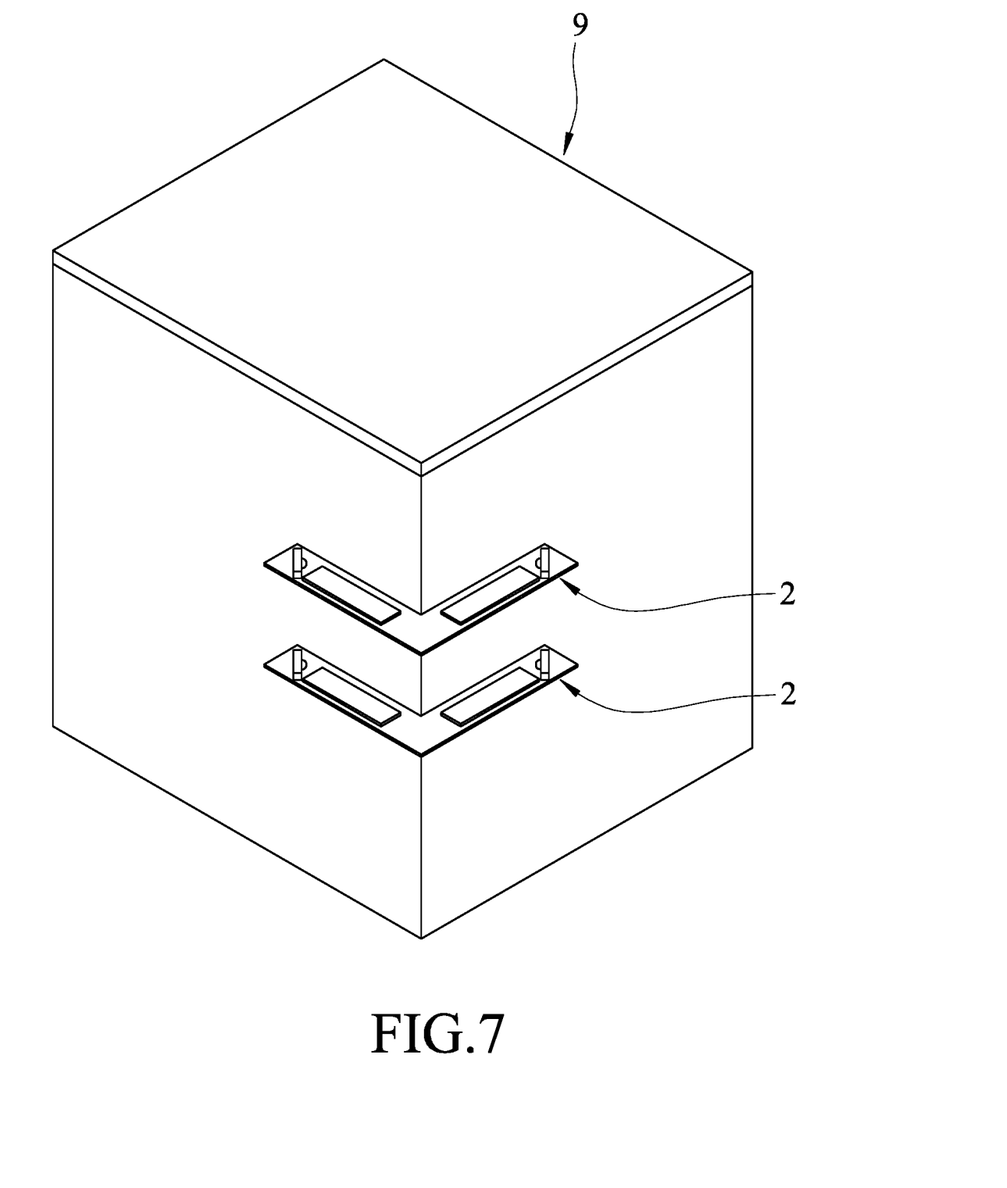
FIG. 7 is a perspective view of the first exemplary embodiment, illustrating multiple detecting devices to be included in the detecting apparatus.
Figure 9:
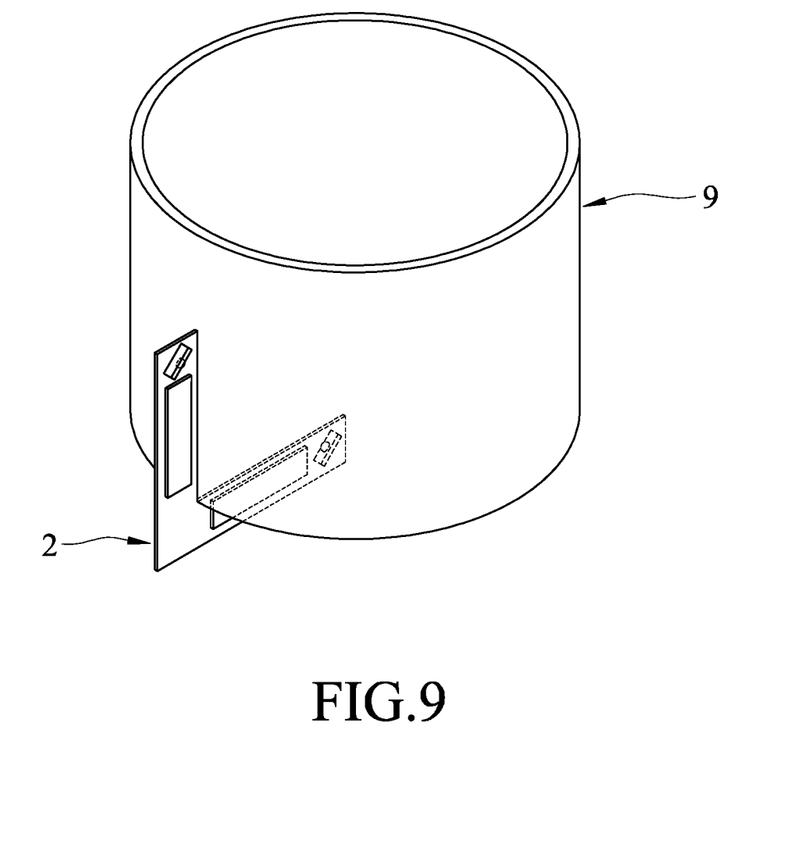
FIG. 9 is yet another perspective view of the first exemplary embodiment.

Here, as shown in FIG. 4, the light-emitting element 31 and the light-receiving element 41 may be respectively provided at first and second points (31P, 41P) of the container 9. Specifically, the light-emitting element 31 may be located on a normal line (L3) of a first imaginary tangent plane (P1) which is tangent to the first point (31P) of the container 9 as shown in FIGS. 4 to 6. Likewise, the light-receiving element 41 may be located on a normal line (L4) of a second imaginary tangent plane (P2) which is tangent to the second point (41P) of the container 9. The first and second points (31P, 41P) may be respectively located at two adjacent side surfaces of the container 9 as illustrated in FIG. 7, or being respectively located at the bottom surface and the side surface of the container 9 as illustrated in FIG. 9. As shown in FIGS. 4 to 6, the first imaginary tangent plane (P1) is not parallel to the second imaginary tangent plane (P2), and may intersect with the second imaginary tangent plane (P2) at an angle (φ) ranging from 45° to 135°. In the first exemplary embodiment, the angle (φ) between the first and second imaginary tangent planes (P1, P2) is identical to the angle (θ) between the indentation-defining planes 211, 221 as shown in FIG. 4, and a distance between the light-emitting element 31 and the light-receiving element 41 is equal to or less than 15 cm.

In the first exemplary embodiment, the transmitting module 3 may further include a collimating lens 33 for collimating the photo signal transmitted from the light-emitting element 31 as illustrated in FIG. 5. The receiving module 4 may also include a collimating lens 43 for collimating the photo signal transmitted toward the light-receiving element 41 as illustrated In FIG. 5.

Figure 8:
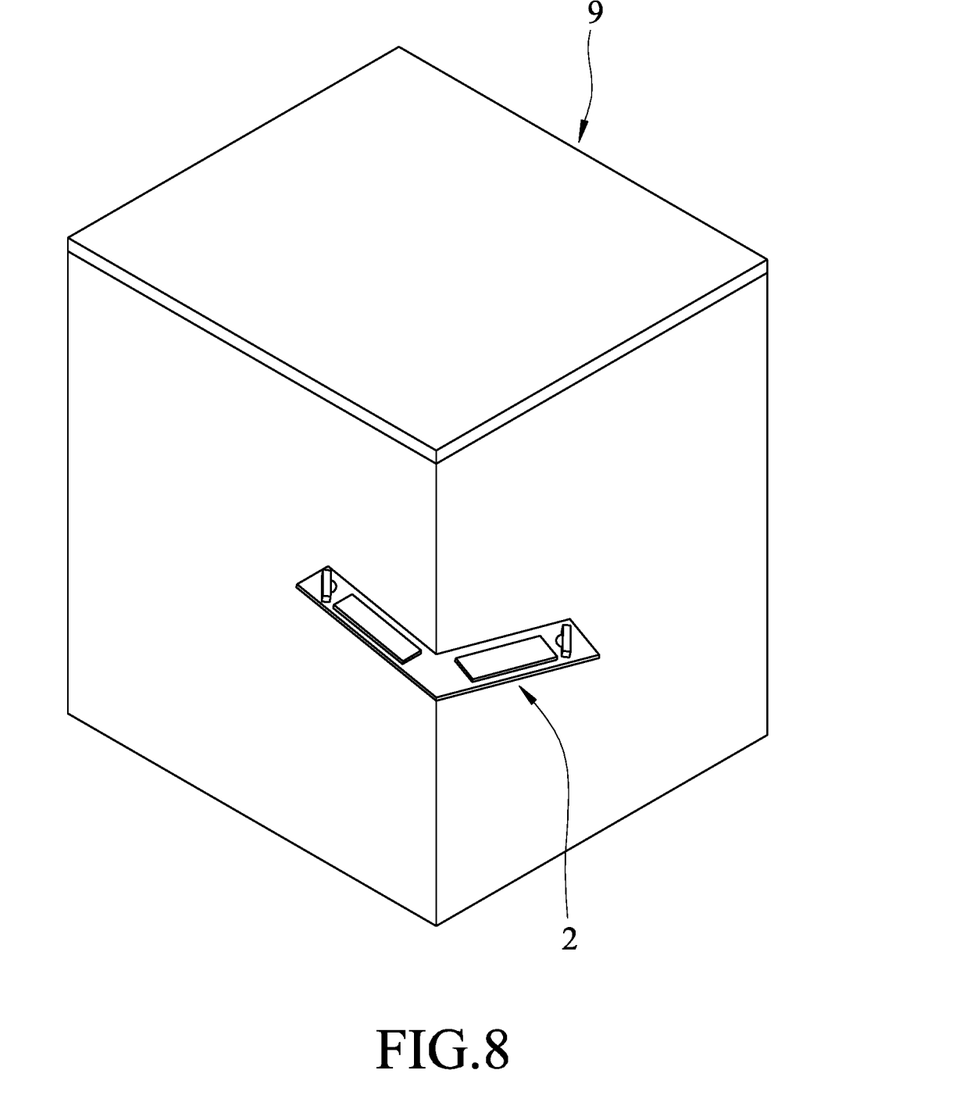
FIG. 8 is another perspective view of the first exemplary embodiment.

It is worth noting that, multiple detecting devices may be included in the detecting apparatus as illustrated in FIG. 7, so as to detect the level or amount of the substance in the container 9. It is also worth noting that, the detecting device may be disposed in a non-horizontal manner as illustrated in FIGS. 8 and 9, so as to have a wider detecting range with respect to the level of the substance in the container 9.

By way of disposing the light-emitting element 31 and the light-receiving element 41 respectively at the first and second points (31P, 41P) of the container 9 which have non-parallel first and second imaginary tangent planes (P1, P2), the detecting device of the present disclosure can be provided at only one side of the container 9 and thus require a relatively small space for installation in comparison to the prior art. Moreover, by disposing the light-emitting element 31 and the light-receiving element 41 respectively at the first and second side segments 21, 22 of the substrate body 2, one may attach the detecting device directly onto the container 9 without the need to calibrate the position of the light-emitting element 31 relative to the light-receiving element 41, thereby effectively reducing the assembly time thereof.

Figure 10:
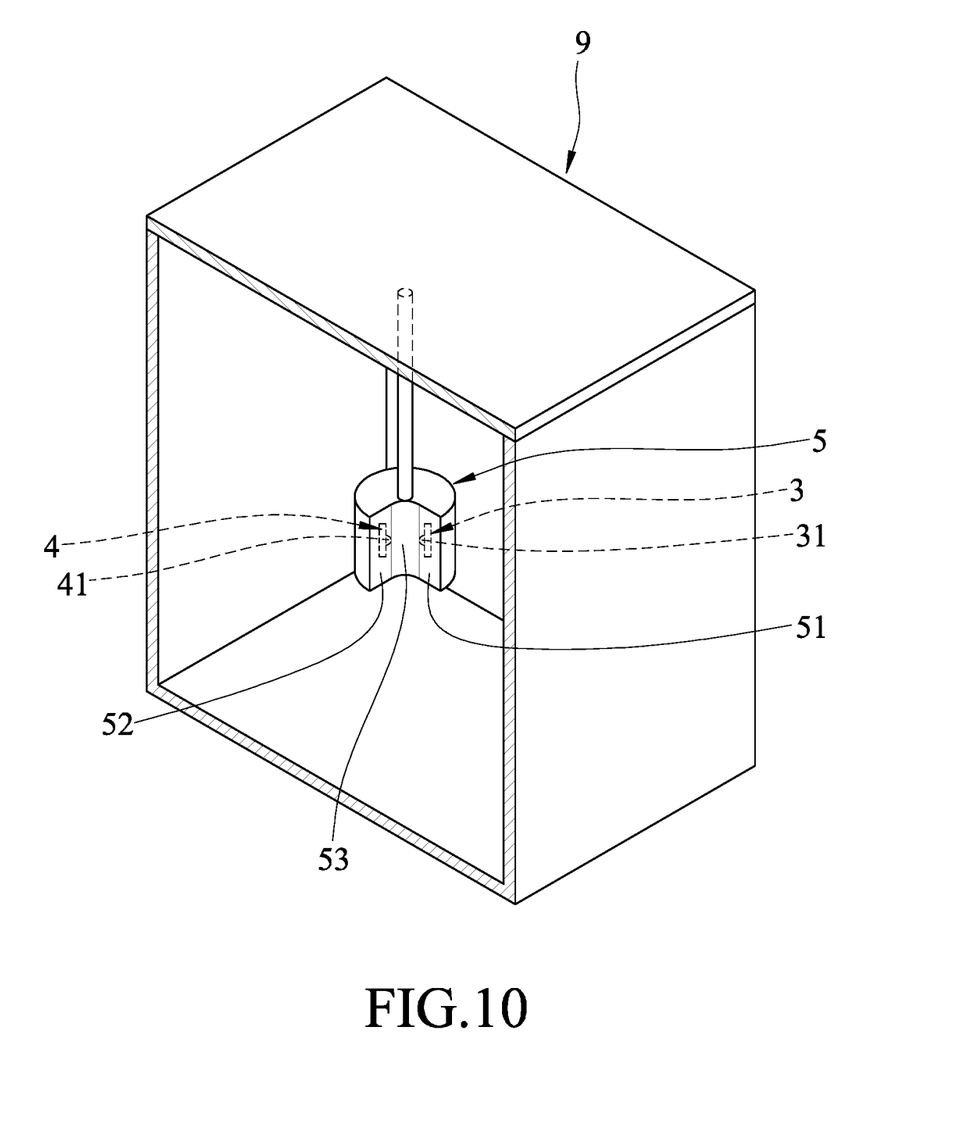
FIG. 10 is a cutaway perspective view, illustrating a second exemplary embodiment of the detecting device according to the present disclosure.

Referring to FIG. 10, a second exemplary embodiment of the detecting device according to the present disclosure is shown to be similar to that of the first exemplary embodiment. The differences between the first and second exemplary embodiments are as follows.

As shown in FIG. 10, the detecting device of the second exemplary embodiment further includes an enclosure 5 that is disposed in the container 9 and that has first and second space-defining planes 51, 52 to cooperatively define a receiving space 53. The light-emitting element 31 is received in the enclosure 5, is provided at the first indentation-defining plane 51, and is operable to transmit the photo signal to propagate toward the receiving space 53 from the first space-defining plane 51. The light-receiving element 41 of the receiving module 4 is received in the enclosure 5, is provided at the second space-defining plane 52 and is configured to receive the photo signal transmitted from the light-emitting element 31 through the receiving space 53, such that the receiving module 4 is operable to determine whether the substance is present in the receiving space 53 based on the receipt of the photo signal by the light-receiving element 41. The first and second space-defining planes 51, 52 may intersect at an angle ranging from 45° to 135°. In one embodiment, the angle may be 90°.

In the second exemplary embodiment, the enclosure is configured into a cylindrical shape and liquidtightly receives the transmitting module 3 and the receiving module 4. It is worth noting that the position where the enclosure 5 is placed in the container 9 is not limited. It is also worth noting that the enclosure 5 may be at least partially light-transmissible, so as to allow the light-emitting element 31 to transmit the photo signal via the first space-defining plane 51, and allow the light-receiving element 41 to receive the photo signal via the second space-defining plane 52.

By virtue of the configuration, the detecting device of the second exemplary embodiment also requires a relatively small space for installation like the first exemplary embodiment, and is suitable for the container 9 of various shapes.

Figure 11:
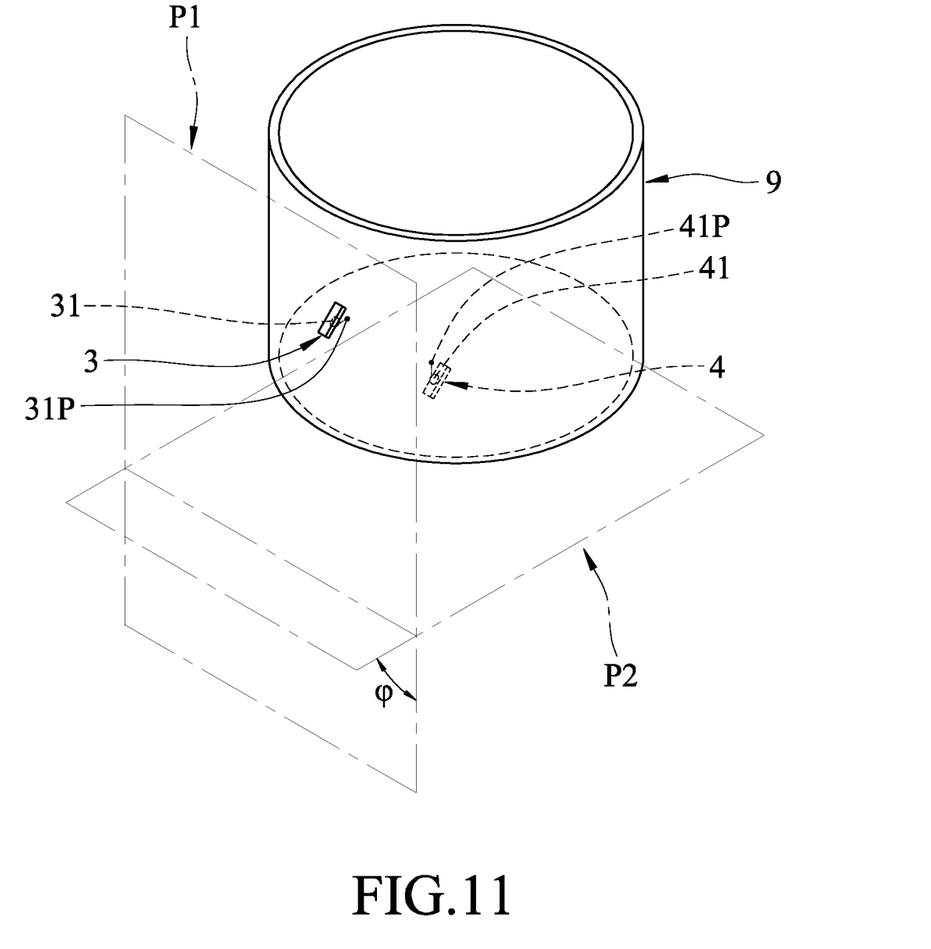
FIG. 11 is a schematic perspective view, illustrating a third exemplary embodiment of the detecting device according to the present disclosure.

Referring to FIG. 11, a third exemplary embodiment of the detecting device is shown to be similar to that of the first exemplary embodiment. The differences between the first and third exemplary embodiments are as follows.

As shown in FIG. 11, the substrate body is omitted in the third exemplary embodiment, i.e., the light-emitting element 31 and the light-receiving element 41 of the third exemplary are separate pieces and are respectively provided at the first and second points (31P, 41P), where the first imaginary tangent plane (P1) tangent to the first point (31P) is not parallel to the second imaginary tangent plane (P2) tangent to the second point (41P) of the container 9 like in the first exemplary embodiment. The method of using the detecting device of the third exemplary embodiment is similar to that of the first exemplary embodiment and includes the steps of:

(a) disposing the light-emitting element 31 at the first point (31P) of the container 9; and (b) disposing the light-receiving element 41 at the second point (41P) of the container 9, where the first imaginary tangent plane (P1) tangent to the first point (31P) of the container 9 is not parallel to the second imaginary tangent plane (P2) tangent to the second point (41P) of the container 9.

Like in the first exemplary embodiment, the first and second points (31P, 41P) may be respectively located at two adjacent side surfaces of the container 9, or respectively located at the bottom surface and one of the side surfaces of the container 9. Also, the first imaginary tangent plane (P1) may intersect with the second imaginary tangent plane (P2) at the angle ($\varphi$) ranging from 45° to 135°.

It is also worth noting that the light-emitting element 31 and the light receiving element 41 may be disposed at an inner side of the container 9. By such, the container 9 may not need to be light transmissive.

The detecting device of the third exemplary embodiment, as well as the method of using the same, has the advantages similar to those of the first exemplary embodiment.

In the description above, for the purposes of explanation, numerous specific details have been set forth in order to provide a thorough understanding of the embodiment(s). It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects.

While the disclosure has been described in connection with what is (are) considered the exemplary embodiment(s), it is understood that this disclosure is not limited to the disclosed embodiment(s) but is intended to cover various arrangements included within the spirit and scope of the broadest interpretation so as to encompass all such modifications and equivalent arrangements.

What is claimed is:

1. A detecting apparatus, comprising:
    a container for receiving a substance; and
    a detecting device including
        a transmitting module including a light-emitting element that is provided at a first point of said container and that is operable to transmit a photo signal to propagate toward said container along an optical path, and
        a receiving module including a light-receiving element that is provided at a second point of said container and that is configured to receive the photo signal transmitted through said container along the optical path,
    wherein said receiving module is operable to determine whether the substance is present in the optical path within said container based on receipt of the photo signal by said light-receiving element,
    wherein a first imaginary tangent plane tangent to said first point of said container is not parallel to a second imaginary tangent plane tangent to said second point of said container, and
    wherein said detecting device further includes a substrate body having two side segments that cooperatively define a V-shaped indentation, said light-emitting element being provided at one of said side segments and operable to transmit the photo signal toward said V-shaped indentation, said light-receiving element being provided at the other one of said side segments and facing said V-shaped indentation.

2. The detecting apparatus of claim 1, wherein said side segments of said substrate body respectively have indentation-defining planes intersecting at an angle ranging from 45° to 135°.

3. The detecting apparatus of claim 2, wherein said angle is 90°.

4. The detecting apparatus of claim 1, wherein said substrate body is configured into an L-shaped structure.

5. The detecting apparatus of claim 1, wherein said substrate body is integrally formed as one piece.

6. The detecting apparatus of claim 1, wherein a distance between said light-emitting element and said light-receiving element is equal to or less than 15 cm.

7. The detecting apparatus of claim 1, wherein:
    said transmitting module further includes a control element that is electrically coupled to said light-emitting element and that is operable to control said light-emitting element to transmit the photo signal; and said receiving module further includes a control element that is electrically coupled to said light-receiving element and that is operable to determine the presence of the substance upon the receipt of the photo signal by said light-receiving element.

8. The detecting apparatus of claim 1, wherein said transmitting module further includes a collimating lens for collimating the photo signal transmitted from said light-emitting element.

9. The detecting apparatus of claim 1, wherein said receiving module further includes a collimating lens for collimating the photo signal transmitted toward said light-receiving element.

10. The detecting apparatus of claim 1, wherein said container has a bottom surface and at least one side surface, one of said first and second points being located at said bottom surface, the other one of said first and second points being located at said at least one side surface.

11. The detecting apparatus of claim 1, wherein said container has a plurality of side surfaces, said first and second points being respectively located at adjacent two of said side surfaces.

12. The detecting apparatus of claim 1, wherein said first and second imaginary tangent planes intersect at an angle ranging from 45° to 135°.

13. The detecting apparatus of claim 11, wherein the angle is 90°.

14. A method for detecting presence of a substance in a container, comprising:
providing a detecting device including
a substrate body having two side segments that cooperatively define a V-shaped indentation,
a transmitting module including a light-emitting element that is provided at one of the side segments, and that is operable to transmit a photo signal toward the V-shaped indentation, and
a receiving module including a light-receiving element that is provided at the other one of the side segments that faces the V-shaped indentation, and that is configured to receive the photo signal;
disposing the light-emitting element at a first point of the container; and
disposing the light-receiving element at a second point of the container in such a manner that a first imaginary tangent plane tangent to the first point of the container is not parallel to a second imaginary tangent plane tangent to the second point of the container.

15. The method of claim 14, wherein the first point is located at a bottom surface of the container, and the second point is located at a side surface of the container.

16. The method of claim 14, wherein the first and second points are respectively located at two adjacent side surfaces of the container.

* * * * *